(12) United States Patent
Aoki

(10) Patent No.: US 7,682,351 B2
(45) Date of Patent: Mar. 23, 2010

(54) METHOD FOR INFUSING INSULIN TO A SUBJECT TO IMPROVE IMPAIRED HEPATIC GLUCOSE PROCESSING

(76) Inventor: Thomas T. Aoki, 1021 El Sur Way, Sacramento, CA (US) 95864

( * ) Notice: Subject to any disclaimer, the term of this patent is extended or adjusted under 35 U.S.C. 154(b) by 1260 days.

(21) Appl. No.: 10/738,897

(22) Filed: Dec. 17, 2003

(65) Prior Publication Data

US 2005/0137572 A1 Jun. 23, 2005

(51) Int. Cl.
*A61M 31/00* (2006.01)
(52) U.S. Cl. ....................................... 604/504
(58) Field of Classification Search ................ 604/500, 604/65–67, 503, 504, 507
See application file for complete search history.

(56) References Cited

U.S. PATENT DOCUMENTS 4,826,810 A * 5/1989 Aoki .............................. 514/3

\* cited by examiner

*Primary Examiner*—Nicholas D Lucchesi
*Assistant Examiner*—Theodore J Stigell
(74) *Attorney, Agent, or Firm*—Eric G. Masamori

(57) ABSTRACT

The present invention is a method for delivering insulin to a subject to improve impaired hepatic glucose processing. The method delivers a series of pulses of insulin to the subject over a period of time accompanied by ingestion of glucose in the form of a carbohydrate containing meal. The amount of insulin in each pulse, the interval between pulses and the amount of time to deliver each pulse to the subject are selected so that the hepatic processing of glucose is restored in the subject. In subjects whose hepatic glucose processing has been restored there is a subsequent fall in circulating blood glucose levels of 50 mg/dl or more directly as a result of improved hepatic glucose processing.

9 Claims, No Drawings

METHOD FOR INFUSING INSULIN TO A SUBJECT TO IMPROVE IMPAIRED HEPATIC GLUCOSE PROCESSING

FIELD OF INVENTION

The present invention is a method for delivering a series of pulses of insulin over a period of time to a subject to improve impaired hepatic glucose processing. More specifically, the amount of insulin in each pulse, the interval between pulses and the amount of time to deliver each pulse to the subject are selected such that the subject's hepatic processing of glucose is restored. In subjects whose hepatic glucose processing has been restored there is a subsequent fall in circulating blood glucose levels of 50 mg/dl or more directly as a result of hepatic glucose processing being restored to the liver.

BACKGROUND OF THE INVENTION

Diabetic retinopathy is a major cause of blindness. While earlier detection and major advances in laser therapies have made significant impact on this chronic complication of diabetes, the number of diabetic patients suffering from diabetic retinopathy continues to increase.

Glucose control is typically measured by a blood test, which determines the level of hemoglobin A1c, which has been the desired result of insulin therapy in diabetic patients for many years. However, it is clear that tight circulating glucose control was insufficient in 25% or more of the study participants to protect them from the onset or progression of diabetic retinopathy, nephropathy or neuropathy.

A major cause of death for patients with diabetes mellitus is cardiovascular disease in its various forms. Existing evidence indicates that diabetic patients are particularly susceptible to heart failure, primarily in association with atherosclerosis of the coronary arteries and autonomic neuropathy. There is little doubt that a metabolic component is present in various forms of cardiovascular disease in diabetic patients. Cardiac dysfunction (lower stroke volume, cardiac index and ejection fraction and a higher left ventricular end diastolic pressure) frequently manifested by patients with diabetes, can be explained at least partially by metabolic abnormalities, and is likely secondary to insulin deficiency since appropriate insulin administration can restore normal patterns of cardiac metabolism (Avogaro et al, Am J Physiol 1990, 258:E606-18).

The pathophysiology of diabetic nephropathy is only partially understood. The most consistent morphologic finding in diabetic nephropathy is the enlargement of the mesangium, which can compress the glomerular capillaries and thus alter intraglomerular hemodynamics.

Diabetes is the number one cause of non-traumatic amputations. The common sources of amputations are wounds that will not heal and progress to necrosis and gangrene. It is generally observed that diabetic patients have greater difficulty in healing and in overcoming infections. Diabetes in general and poor circulating glucose control in particular are thought to be causally related to poor wound repair in diabetic patients. Poor circulating glucose control is also a source of a lack of energy and a general feeling of malaise.

As reported in *Diabetes mellitus and the risk of dementia* A. Ott, R. P. Stolk, F. Van Harskamp, The Rotterdam Study, Neurology, 1999, vol. 53, pp. 1937-1942, patients with diabetes have an increased risk of dementia. Having diabetes almost doubled the risk of having dementia (the risk was 1.9 times greater). The risk of diabetics getting Alzheimer's disease was also nearly double. And in diabetics taking insulin, the risk was over 4 times that in non-diabetics. Even after adjusting for possible effects of sex, age, educational level and the other factors measured, the findings were the same. Therefore, it can be concluded that diabetes is a risk factor for the development of dementias, including Alzheimer's disease.

What is needed is a method which can restore metabolism; increase retinal and neural glucose oxidation by enhancing pyruvate dehydrogenase activity; treat retinopathy and central nervous system disorders; increase stroke volume, that improves cardiac index; increases ejection fraction, and that lowers ventricular end diastolic pressure, thus improving cardiac function, as well as improving the quality of life in diabetic patients. A similar method is also needed to significantly reverse the cardiac dysfunction common to diabetic patients with heart disease. The same method should be capable of providing improved blood glucose control as measured by hemoglobin A1c. Additionally a similar method is needed to improve the entire metabolic process and through its multiplicity of effects on neurovascular reactivity, intraglomerular pressure and hemodynamics, arrest the progression of overt diabetic nephropathy, improve intraglomerular hemodynamics, and thus arrest the progression of diabetic nephropathy and reduce the risk of development of End-Stage Renal Disease (ESRD). Further a similar method is also needed to increase glucose oxidation in the affected areas and therefore provide more energy for the same amount of oxygen delivered for treating wounds, promote healing and avoid lower extremity amputations in both diabetic and non-diabetic patients. A method is required to improve the metabolism in the brain of patients suffering with any of a number of diseases causing senile dementia and hence improve mental function of patients suffering senile dementia.

In a previous patent, U.S. Pat. No. 4,826,810, which is hereby incorporated in the description of this invention, the inventor describes a method of delivering pulses of insulin to a patient after ingestion of a glucose containing meal. The pulses of insulin are adjusted to produce a series of peaks in the free insulin concentration so that successively there are increasing free insulin concentration minima between the said peaks. In order to make this a viable treatment for clinical purposes there needs to be a simple, low-cost way of measuring free insulin to determine said peaks to insure that the correct levels are present to insure that the dietary carbohydrate processing capabilities of the subject's liver are activated. The only viable method for measuring "free" insulin is costly and time consuming, often taking days to obtain results. In the mean time it is not known whether or not the liver has been activated. What is needed is a way to determine, in real time while pulses are being administered and the base line of free insulin is rising, that in fact the patient's liver has been activated.

SUMMARY OF THE INVENTION

According to the present invention is a method for delivering insulin to a subject to improve impaired hepatic glucose processing. The method delivers a series of pulses of insulin to the subject over a period of time accompanied by ingestion of glucose in the form of a carbohydrate containing meal. The amount of insulin in each pulse, the interval between pulses and the amount of time to deliver each pulse to the subject such as a patient are selected so that the hepatic processing of glucose is restored in the subject.

Coincident with or shortly following the establishment of elevated circulating glucose levels in the patient, the first pulse of insulin delivery is administered. This pulse of insulin results in a peak "free" insulin concentration in the blood. When the "free" insulin concentration decreases by about 50%, a second pulse of insulin is administered. When the "free" insulin concentration again decreases by about 50% the next pulse of insulin is administered. Repetition of this process will result in increasing interpeak "free" insulin concentration. The pulses of insulin are regulated so that the interpeak "free" insulin concentration increases by 10 to 500 µU/ml from one pulse to the next. In order to activate the liver, an increasing interpeak "free" insulin concentration after ingestion of a carbohydrate containing meal is required to activate the liver and for the circulating blood glucose level to drop 50 mg/dl in subjects with impaired hepatic glucose processing. However, there are times that even though the interpeak "free" insulin levels are rising, they do not rise sufficiently fast to activate the liver. In those circumstances the drop in circulating glucose will not fall by 50 mg/dl or more.

It is desirable to administer the least amount of insulin consistent with activation of the hepatic glucose processing. However, the amount of insulin required to activate a patient will vary from patient to patient or even from day to day in the same patient. For the same patient on one day a pulse regimen will be successful in activation of hepatic glucose processing while the same patient on the following day may require significantly more insulin per pulse or more frequent pulses to attain activation. Measuring "free" insulin levels in the blood is an expensive and time-consuming procedure, which cannot provide the necessary information in real time. The current invention is a method to measure in real time when the patient has actually activated hepatic glucose processing allowing positive confirmation of successful patient response and signaling when the pulses no longer need to be administered.

In subjects whose hepatic glucose processing has been restored there is a subsequent fall in circulating blood glucose levels of 50 mg/dl or more directly as a result of hepatic glucose processing being restored to the liver. This circulating glucose signal is easy and low cost to obtain, can be done by the patient easily in a home health care environment under the supervision of a doctor, and provides information in real time that, for example, the liver's ability to oxidize glucose is restored. Patients are usually well trained and fully capable of obtaining their own circulating glucose levels without the need of a doctor to assist with the procedure and evaluate the results. Other means to determine whether the liver has been activated are costly, do not provide information in real time, require a doctor's evaluation or cannot be used in a home health care environment. There must be more than a minimum of two pulses in the series of insulin pulses; for example, three, four, five or six. In the preferred embodiment of the method an infusion device delivers a series of ten pulses over a period of one hour. The infusion device is preferably controlled by a programmable processor unit, which controls the amount of insulin in each pulse, the time to deliver each pulse, and the time between pulses. Circulating blood glucose levels can be measured by any appropriate circulating glucose measuring method including finger stick methods.

DESCRIPTION OF PREFERRED EMBODIMENTS

Accordingly, the present invention is a method for delivering a series of pulses of insulin over a period of time to a subject to improve impaired hepatic glucose processing. The amount of insulin in each pulse, the interval between pulses and the amount of time to deliver each pulse to the subject are selected such that hepatic processing of glucose is restored in the subject. The pulses of insulin are accompanied by the ingestion of glucose in the form of a carbohydrate containing meal. Circulating glucose measurements are made periodically to insure proper hepatic processing of glucose has been restored. In subjects whose hepatic glucose processing has been restored there is a subsequent fall in circulating blood glucose levels of 50 mg/dl or more directly as a result of improved hepatic glucose processing.

Hepatic processing of glucose includes proper uptake of glucose in the liver cells, oxidation of glucose by the liver cells, storage of glucose as hepatic glycogen in the liver cells, and conversion of glucose to fat or alanine, an amino acid, by the liver cells. Hepatic processing is impaired when the liver fails to produce hepatic enzymes (specifically hepatic glucokinase, phosphofructokinase, and pyruvate kinase) needed in proper glucose processing. Impaired processing of glucose is a fundamental condition of type 1 and type 2 diabetic patients, for patients whose pancreas is not producing sufficient insulin, and for patients experiencing significant insulin resistance, or a combination of these factors. After the ingestion of glucose, even with intravenous insulin administration, decreased glucose oxidation, low alanine production, and little glycogen formation and deposition in the liver in a timely manner are all indications that hepatic glucose processing is impaired. Glucose tolerance tests and measurements of hemoglobin A1c can be used as indications that hepatic processing of glucose has been impaired.

The preferred embodiment of the method for delivering insulin pulses to a patient to improve impaired hepatic glucose processing is as follows. On the morning of the procedure, the patient is preferably seated in a blood drawing chair and a 23 gauge needle or catheter is preferably inserted into a hand or forearm vein to obtain vascular access. However, any system of such access may accomplish the needed result, including indwelling catheters, PICC lines and PORTA-CATHS. After a short equilibration period, the patient is asked to make a circulating glucose measurement prior to starting the actual infusion of insulin. A steady baseline circulating glucose level is achieved when two identical consecutive measurements taken 5 minutes apart is obtained. It is preferable that patients have circulating glucose levels close to 200 mg/dl prior to using the infusion method. In the case of pregnant diabetic women, however, every attempt is made to keep the maximum circulating glucose level to 150 mg/dl or less.

After the circulating glucose measurement has been taken and the patient has the proper circulating glucose starting level, the patient is asked to consume a liquid or food containing glucose. The amount of glucose given to s diabetic patient ranges from 60 to 100 grams, but for small framed people the amount could be as low as 40 grams of glucose. However, the amount of initial glucose given to the patient may vary. Liquid or food containing glucose is consumed by the patient to prevent the patient from becoming hypoglycemic. The preferred liquid or food is GLUCOLA, but any similar type of liquid or high glycemic food, including but not limited to cake and bread, containing glucose may be given to the patient. In a non-diabetic patient more glucose may be required than in the diabetic patient, but the other parameters would remain the same, including the need for a pulsed delivery of insulin.

Pulses of insulin are then administered intravenously at planned intervals of time, usually every six minutes. However other intervals may be used from as low as every three minutes up to every 30 minutes. For diabetic patients the amount of insulin in each pulse is 10-200 milliunits of insulin per kilogram of body weight; for non-diabetic patients the amount of insulin in each pulse is slightly lower.

In the preferred embodiment of the invention, a programmable insulin infusion device is used to deliver intravenous insulin in precisely measured pulses. However, any method of infusing measured amounts of insulin may be used, including simple injection with a syringe. It is preferable that the infusion device be capable of providing measured pulses of insulin on a prearranged interval, so long as there is sufficient glucose in the blood to keep the patient from becoming hypoglycemic. It is also preferable that the infusion device is capable of delivering the pulses of insulin in as short duration of time as possible, without adversely affecting the vein at the site of infusion is used. One preferred infusion device is the BIONICA MD-110. However, less accurate devices and slower devices, including a simple syringe, may deliver the pulses of insulin to achieve the needed infusion profile. In the preferred embodiment, there must be more than a minimum of two pulses in the series of insulin pulses; for example, three, four, five or six. In the preferred embodiment of the method an infusion device delivers a series of ten pulses over a period of one hour.

In the preferred insulin infusion device, programmed values can be input to a control processor via a keyboard, through firmware in the infusion device or by software via a communications link from a higher level computer or any other appropriate input method. Automated entry of blood glucose levels is also desired. The communications link may also be used to send alarm and status messages to a higher level computer via any acceptable communications protocol and medium. Infusion device status, alarm status and circulating-glucose levels, among other parameters of the system may be displayed on a display panel of the infusion device.

A circulating glucose measuring instrument, configured to communicate directly with the infusion device through the communications link can provide timely values of circulating glucose. Alternatively, wireless communications systems can send information from a circulating glucose sensor automatically to the infusion device without operator intervention. Typical circulating glucose sensors include but are not limited to finger stick devices, non-invasive instruments using near infrared spectroscopy or radio frequency, and implanted sensors. Alternatively the circulating glucose signal can come from an implantable system for monitoring pancreatic beta cell electrical activity in a patient in order to obtain a measure of a patient's insulin demand and circulating glucose level. Any other method for either directly or indirectly obtaining an accurate measure of the change in circulating glucose levels is also acceptable. The communications link may also be used to send alarm and status messages to a higher level computer via any acceptable communications protocol and medium.

When the infusion device is activated, it dispenses the programmed pulse of insulin in the programmed amount of time to the subject. The insulin travels through an infusion tube into a needle that is inserted intravenously into the subject's forearm. The intravenous site can also be any convenient location such as the body or hand. The time to deliver each pulse should be as short as possible and at least less than one minute and preferably on the order of seconds. The infusion device status, alarm status and circulating-glucose levels, among other parameters of the method may be displayed on a display panel.

In the preferred embodiment the subject's circulating glucose levels are measured as frequently as possible. The measurements are either automatically or manually input into the preferred infusion device. Adjustments to ingested glucose and infused insulin are made to produce the desired results of activating the liver without the unwanted side effects of either hypoglycemia or hyperglycemia.

When finger pricks are used to determine the circulating glucose level it is recommended that readings be taken every 30 minutes. When less invasive methods of measuring circulating glucose are used readings can be taken more frequently, preferably after the infusion of each pulse of insulin. It is recommended that a period of one to two minutes is allowed after the infusion of each pulse of insulin before circulating glucose levels are measured. In patients whose hepatic glucose processing has been restored there may be a fall in circulating glucose levels by as much as 50-100 mg/dl by the third treatment. In patients who have yet to obtain proper hepatic glucose processing, there will be no fall or a fall considerably less than 50 mg/dl by the third treatment. The fall in circulating glucose levels, indicating restoration of hepatic processing of glucose, is generally achieved within one hour of initiation of the first pulse of insulin using the preferred embodiment of this invention; however, the time required may be shorter or longer than one hour. It is possible to decrease the amount of insulin in each pulse and to lengthen the time between pulses so that it takes in excess of two or even three hours or more for a fall of 50 mg/dl to occur. The longer the time it takes to activate the patient, however, the longer the patient must be under treatment and the less desirable the treatment is for the patient. This decrease in circulating glucose level is caused by the combination of increased glucose utilization by muscles and the use of glucose by the liver.

Another indication that hepatic activation of the liver has been reestablished is that gradually the amount of insulin required to reduce the circulating glucose levels by 50 mg/dl or more will decrease with time. Lowering hemoglobin A1c levels are a more mid-term manifestation that hepatic processing has been restored. Longer-term manifestations are seen in the decrease of a number of complications related to diabetes, including but not limited to retinopathy, nephropathy, neuropathy, hypoglycemia, cardiovascular disease, and hypertension.

The phase during which a series of pulses of insulin is administered and glucose ingested lasts typically for 56 minutes (ten pulses with a six minute interval between pulses) and is followed by a rest period of usually one or two hours. The rest period allows the elevated insulin levels to return to baseline. During periods when insulin is not being infused, the intravenous site is preferably converted to a heparin or saline lock. The entire procedure is repeated until the desired effect is obtained. Typically the procedure is repeated three times for each treatment day, but can be repeated as few as two times and up to 8 times in one day. Prior to the patient being discharged from the procedure, whether in the clinic or home environment, in the preferred embodiment circulating glucose levels stabilize at 100-200 mg/dl for approximately 3045 minutes.

Coincident with or shortly following the establishment of elevated circulating glucose levels in the patient, the first pulse of insulin delivery is administered. This pulse results in a peak "free" insulin concentration in the blood. When the "free" insulin concentration decreases by about 50%, a second pulse of insulin is administered. The concentration of "free" insulin will rise as a result of the second pulse of insulin. When the "free" insulin concentration again decreases by about 50%, the next pulse of insulin is administered. Repetition of this process will result in increasing interpeak "free" insulin concentration. The pulses of insulin are regulated so that the interpeak "free" insulin concentration increases by 10 to 500 μU/ml from one pulse to the next.

In order to activate the liver, an increasing interpeak "free" insulin concentration after ingestion of a carbohydrate containing meal is required to activate the liver and for the circulating blood glucose level to drop 50 mg/dl in subjects with impaired hepatic glucose processing. However, there are times that even though the interpeak "free" insulin levels are rising, they do not rise sufficiently fast to activate the liver. In those circumstances the drop in circulating glucose will not reach 50 mg/dl.

It is desirable to administer the least amount of insulin consistent with activation of the hepatic glucose processing. However, the amount of insulin required to activate a patient will vary from patient to patient or even from day to day in the same patient. For the same patient on one day a pulse regimen will be successful in activation of hepatic glucose processing while the same patient on the following day may require significantly more insulin per pulse or more frequent pulses to attain activation. Measuring "free" insulin levels in the blood is an expensive and time-consuming procedure, which cannot provide the necessary information in real time. The current invention is a method to measure in real time when the patient has actually activated hepatic glucose processing, to allow positive confirmation of successful patient response and signal when the pulses no longer need to be administered.

Accordingly, the present invention is used to increase retinal and neural glucose oxidation by enhancing pyruvate dehydrogenase activity and therefore treats retinopathy and central nervous system disorders in both diabetic and non-diabetic patients. One method of monitoring retinal and neural glucose oxidation is PET (Positron Emission Tomography) scans. Alternatively, one may look for stabilization/reversal of diabetic retinopathy. In terms of neural function, there will be improvement in peripheral neuropathy manifested as increased perception of sensation, especially in the feet, and a loss of the painful "burning" or "pins and needles" sensation in the feet. There will also be improvement in autonomic neuropathy, especially gastroparesis and improvement in postural or orthostatic hypotension.

Diabetic heart disease is the one of the more common complications of diabetes, experienced by both type I and type II diabetic patients. Experts generally agree that the primary fuel for both the normal and diabetic heart is free fatty acids, a fuel that requires more oxygen on a per calorie basis than glucose as a fuel. As a consequence, the heart of both diabetic and non-diabetic individuals is particularly vulnerable to ischemia. If the involved tissue had been primarily utilizing free fatty acids for energy generation, even a slight or temporary decrease in blood flow or oxygen supply would be catastrophic. On the other hand, if that tissue had been oxidizing glucose rather than free fatty acids, for the generation of an equivalent amount of energy, a temporary disruption of blood or oxygen supply would not be as deleterious, since that tissue's oxygen requirements would be less. Thus, for the same amount of oxygen delivered to the myocardium, glucose utilization rather than free fatty acid utilization would result in increased energy (ATP) generation. The present invention is capable of improving the dietary fuel processing capabilities by allowing for more glucose to be burned or oxidized and correcting over utilization of free fatty acids associated with heart disease and cardiovascular disease in both diabetic and non-diabetic patients.

Still further, the present invention is capable of improving the entire metabolic process, and, through its multiplicity of effects on neurovascular reactivity, intraglomerular pressure and hemodynamics, of arresting the progression of overt diabetic nephropathy, of improving intraglomerular hemodynamics, thus arresting the progression of diabetic nephropathy, and reducing the risk of development of ESRD in both diabetic and non-diabetic patients.

Further, the present invention is capable of increasing glucose oxidation in an affected area and thereby providing more energy with the same oxygen delivery for treating wounds, promoting healing and avoiding amputations in both diabetic and non-diabetic patients. The rationale for this improved healing is that the tissue surrounding the affected area suffers from inadequate blood supply, leading to insufficient oxygenation. When this tissue is fueled through enhanced glucose oxidation in lieu of free fatty acid utilization, thereby switching from a predominantly lipid based fuel economy to one based more on glucose oxidation, more energy is available for wound healing for the same amount of blood flow and hence, more healing from the amount of oxygen delivered. In addition, the ability to achieve more energy from less oxygen, thereby addresses a general malaise associated with diabetic individuals who have energy levels which are less than normal.

On many occasions patients who have been diabetics as well as having dementia have been treated with the method of the current invention. Dementia appears to be related to poor metabolism of glucose in the brain, which may well be the result of constricted flow of blood. This poor metabolism is at least in part the cause of the dementia. Use of the present invention in patients suffering from senile dementia has clearly shown improvement in confusion, weakness, disorientation, cognitive function and lack of memory associated with dementia as well as improvement in the blood glucose management. Constricted flow of blood to the brain is also prevalent in demented patients without diabetes and the method of the current invention provides improved metabolism as well to those patients and hence is effective in treating both demented patients with and without diabetes.

In the preferred embodiment, with a new patient two successive days of three treatments are performed the first week. For continuing patients the procedure is performed once a week. For patients who need/require a more intensive approach, the procedure may be repeated 3 or more times, including continuously, each week until the desired clinical outcome is achieved.

The following non-limiting examples are given by way of illustration only.

Example 1

A study was conducted to assess the effects of Chronic Intermittent Intravenous Insulin Therapy (CIIIT) on the progression of diabetic nephropathy in patients with type 1 diabetes mellitus (DM). This 18-month multi-center, prospective, controlled study involved 49 type 1 DM patients with nephropathy who were following the Diabetes Control and Complications Trial (DCCT) intensive therapy (IT) regimen. Of these, 26 patients formed the control group C, which continued on IT, while 23 patients formed the treatment group (T) and underwent, in addition to IT, weekly CIIIT. All study patients were seen in clinic weekly for 18 months, had monthly glycohemoglobin HbA1c checked, and every 3-months urinary protein excretion and creatinine clearance (CrCl) determinations. CrCl declined significantly in both groups as expected, but the rate of CrCl decline in the T group ($2.21 \pm 1.62$ ml/min/yr) was significantly less than in the C group ($7.69 \pm 1.88$ ml/min/yr, $P = 0.0343$). The conclusion is that when CIIIT is added to IT in type 1 DM patients with overt nephropathy, it appears to markedly reduce the progression of diabetic nephropathy.

Example 2

A middle-aged woman with Type 1 diabetes for more than 22 years suffered from polyneuropathy. She had generalized pain and was unable to walk or even wear stockings because of the pain. After receiving treatment with the subject method the pain has been reduced to the point where the woman enjoys rigorous exercise such as roller blading.

Example 3

A middle-aged woman with Type 1 diabetes for more than 30 years had severe peripheral neuropathy, was in constant pain below the knees and had difficulty sleeping at night. After receiving treatment with the subject method, she no longer takes pain medication and has no twinges of pain in her legs. She has been using the treatment for eight years.

Example 4

A middle-aged woman with type 2 diabetes for 17 years was suffering from severe dilated cardiomyopathy (ejection fraction 14-19%). She was placed on the list to receive a heart transplant prior to starting treatment with the subject method. After receiving treatment, the subject reduced her insulin intake from 150 units a day to 24-26 units/day, and she stabilized to the point where she no longer required a heart transplant and, indeed, was removed from the heart transplant list. The patient has been receiving treatment for 10 years and is still off the heart transplant list. Her ejection fraction is currently 29-32%.

Example 5

A middle-aged male with type 1 diabetes for 38 years suffered from macular degeneration (retinopathy). He was unable to drive at night. After receiving treatment with the subject method, the man's eyesight improved to the point where night driving was no longer a concern. The patient has been receiving treatment for 4 years.

Example 6

A middle-aged type 2 diabetic male patient had severe heart disease including congestive heart failure and severe artereosclerotic heart disease. The patient was scheduled for heart surgery but because of his poor condition, surgeons refused to operate. After using the subject method, the doctors were convinced that he could withstand 4-vessel by-pass surgery. The patient had a normal postoperative recovery, which is virtually unheard of for diabetic patients with his stage of heart disease.

Example 7

An older type 2 diabetic male patient was exercising and had excellent circulating glucose control under intense insulin therapy including 3-4 injections per day of subcutaneous insulin. Even so, his diabetes related kidney disease had progressed to the point where he was discharging 1500 milligrams of protein during a 24-hour period and the rate of increase was 500 milligrams/24 hours/year. After using the subject method, the patient's proteinuria was reduced to 600-800 milligrams/24 hours. He has been using the method for 5 years.

Example 8

An older type 1 diabetic female patient who was diabetic from age 5 years old was scheduled for a coronary artery by-pass graft to correct her diabetes related heart disease. The surgeons were reluctant to operate in the condition she was in because of her advanced diabetes related arteriosclerosis. She was scheduled for a single vessel graft. After using the subject method, her condition improved to the point where the doctors performed two instead of one grafts. She had a normal recovery. She continuing using the subject method for several years after the surgery with no further deterioration in her diabetes related heart disease.

Example 9

An older type 2 diabetic male suffering with autonomic neuropathy had very elevated blood pressure readings of 200/120 despite a rigorous program to regulate his circulating glucose using intensive insulin therapy of 3 to 4 subcutaneous insulin injections daily. As a result of using the subject method, his blood pressure decreased to 120/80. He has been using the method for 5 years.

Example 10

An older type 2 diabetic male patient had one amputated leg as a result of diabetes related ulcers on that leg. He had developed ulcers on the other leg that would not respond to any available therapy and was in danger of losing the other leg to amputation. As a result of using the subject method, the ulcers on his second leg healed, and the leg was saved from amputation. This patient used the subject method for several more years, and no additional ulcers formed.

Example 11

A middle-aged type 1 female diabetic patient had developed severe ulcers on both legs, which would not heal with any available treatment. As a result of using the subject method, the ulcers healed and have never returned. The patient has been using the subject method now for 13 years.

Example 12

A middle-aged type 2 male diabetic patient had proliferative diabetic retinopathy with severe bleeding. Multiple photocoagulation scars made additional photocoagulation impossible. As a result of using the subject method the bleeding stopped, and there was no further deterioration of the retina, preserving what eyesight he had left. The patient has been using the subject method for 5 years, and he has had no further bleeding of the retina and no further photocoagulation.

Example 13

An elder type 2 female diabetic patient had severe painful peripheral neuropathy to the point that she was unable to walk and used a wheelchair. After six months of using the subject method, the pain had subsided to the point where she no longer used a wheelchair. Because of financial reasons, she stopped the therapy. As a result, the neuropathy returned, and she returned to using a wheelchair.

Example 14

A middle-aged type 1 female diabetic patient had severe neuropathy. She was a mother of two children who was bedridden with autonomic neuropathy before using the subject method two years ago. Her muscles had atrophied, she could not digest her food, she had been told that her nerves were dying inside her as a result of her diabetes. She stated that if she had not have two children, she would have taken her life. She had to quit her job, went on disability and was in an out of the hospital very often. She had welts on her head causing hair loss. She had no sensation in her feet, she had constant nausea, and she couldn't sleep at night because of the pain. She had insulin absorption problems and tried all different ways to improve the absorption of insulin into her body. For a number of years she injected herself intramuscularly because she felt that she obtained the best absorption of insulin that way. Since using the subject method she has reversed all of the diseases to the point where she has taken herself off disability and is gainfully employed. She has not been in the hospital since. The numbness in her legs has gone away. If she skips the treatment for a week, she can feel the numbness return to her legs. Her gastroparesis was reversed, and she no longer suffers symptoms. Since using the subject method she has no inpatient medical costs now.

Example 15

A 79 year old female diabetic who was suffering from advanced senile dementia was placed in a nursing home because of excessive confusion, weakness, disorientation and lack of memory. Because the nursing home was not keeping up the strict four shot regimen needed by the patient for her diabetic blood sugar control, the patient's children removed the patient from the nursing home. The attending doctor recommended Hepatic Activation. Once the patient was activated, she returned to a totally independent living style. She had significant improvement in her motor skills, memory, and cognitive function. Hepatic Activation clearly had a positive effect on her senile dementia.

For all of the above listed examples, after the initial few days of treatment, the patients underwent treatment once a week, each treatment day consisting of three infusions of insulin accompanied by ingestion of carbohydrates. The infusion device used to infuse the insulin was the BIONICA MD-110 pump. Typically there were ten pulses given over a period of one hour, and a rest period of one hour was taken between infusions of insulin. The form in which the carbohydrates were ingested changed from time to time and included eating foods of high glycemic index including but not limited to bread and cake. The patients' circulating glucose was measured once every thirty minutes by the finger stick method currently used by most diabetic patients. Circulating glucose levels initially rose by 100-150 mg/dl during the first treatment and then fell between 50 and 100 mg/dl by the second and third treatments indicating that in fact the liver had been activated. Table 1 below summarizes by the above examples the number of units of insulin per pulse administered and the amount of glucose ingested for each series of pulses:

The preferred embodiments described herein are illustrative only, and although the examples given include many specificity's, they are intended as illustrative of only a few possible embodiments of the invention. Other embodiments and modifications will, no doubt, occur to those skilled in the art. The examples given should only be interpreted as illustrations of some of the preferred embodiments of the invention, and the full scope of the invention should be determined by the appended claims and their legal equivalents.

TABLE 1

Summary of the above examples: The number of units of insulin per pulse administered and the amount of glucose ingested for each series of pulses

| Example Number | Number of milliunits of insulin/Kg of body weight per Pulse | Grams of Glucose per Series of Insulin Pulses. |
|---|---|---|
| 1* | 15-195 | 40-100 grams |
| 2 | 30-45 | 50-60 grams |
| 3 | 35-50 | 40-60 grams |
| 4 | 45-60 | 40-60 grams |
| 5 | 30-45 | 50-60 grams |
| 6 | 70-100 | 50-70 grams |
| 7 | 40-60 | 50-70 grams |
| 8 | 15-45 | 50-70 grams |
| 9 | 40-55 | 50-70 grams |
| 10 | 45-60 | 40-60 grams |
| 11 | 15-45 | 50-70 grams |
| 12 | 130-170 | 50-70 grams |
| 13 | 30-60 | 50-70 grams |
| 14 | 30-60 | 50-70 grams |
| 15 | 30-60 | 50-70 grams |

*This study included 23 patients in the treatment group with varying amounts of insulin per pulse and varying ingestion of glucose. Hence general limits of what they used are included.

The invention claimed is:

1. A method for infusing insulin intravenously to a subject to improve impaired hepatic glucose processing comprising the steps of:
   a. determining a baseline circulating glucose level of the subject and obtaining a subsequent circulating glucose level at least every 30 minutes,
   b. having the subject ingest a carbohydrate containing meal to cause a rise in circulating glucose levels,
   c. administering a series of insulin pulses until the rise in circulating glucose levels falls a threshold of at least 50 to 100 milligram per deciliter within two hours of administering an initial pulse of insulin; the series of insulin pulses having an amount of insulin in each pulse, an interval of time between pulses and a total time to deliver the series of pulses;
   d. repeating steps a, b and c at least one more time during a treatment day when said threshold is met;
   e. changing the amount of ingested carbohydrate of step b or changing the amount of insulin in each pulse, the interval of time between pulses or the total time to deliver the series of pulses of step c when said threshold is not met and repeating steps a, b, c and d;
   the threshold of 50 milligrams per deciliter fall in circulating glucose levels being an indicator that the amount of ingested carbohydrate, the amount of insulin in each pulse, the interval of time between pulses, and the total time to deliver the series of pulses is sufficient to achieve an improvement in hepatic glucose processing,
   wherein said method measures in real time when the subject has actually activated hepatic glucose processing allowing positive confirmation of successful patient response.

2. The method of claim 1, wherein the carbohydrate containing meal contains 40 to 100 grams of glucose.

3. The method of claim 1, wherein the amount of insulin in each pulse is 10 to 200 milliunits of insulin per kilogram of body weight of said subject.

4. The method of claim 1, wherein the interval of time between pulses is 3 to 30 minutes.

5. The method of claim 1, wherein the total time to deliver the series of pulses is 6 to 180 minutes.

6. The method of claim 1, wherein the administering the series of insulin pulses is by an intravenous infusion device.

7. The method of claim 1, wherein the administering the series of insulin pulses is by a syringe.

8. The method of claim 1, wherein the amount of insulin in each pulse, the interval of time between pulses and the total time to deliver the series of insulin pulses to the subject are controlled by a programmable processor unit of an intravenous infusion pump.

9. The method of claim 8, wherein the step for obtaining the subsequent circulating glucose levels and the step for administering the series of insulin pulses are coordinated through a communications link between a circulating blood glucose sensor and said programmable processor unit of the intravenous infusion pump.

* * * * *

UNITED STATES PATENT AND TRADEMARK OFFICE
CERTIFICATE OF CORRECTION

| | | |
|---|---|---|
| PATENT NO. | : 7,682,351 B2 | |
| APPLICATION NO. | : 10/738897 | |
| DATED | : March 23, 2010 | |
| INVENTOR(S) | : Thomas T. Aoki | |

It is certified that error appears in the above-identified patent and that said Letters Patent is hereby corrected as shown below:

Column 6
Line 53 states "3045", it should read -- 30-45 --.

Signed and Sealed this
Second Day of August, 2011

David J. Kappos
*Director of the United States Patent and Trademark Office*